(12) United States Patent
Boyaval et al.

(10) Patent No.: US 12,042,645 B2
(45) Date of Patent: Jul. 23, 2024

(54) DELIVERY DEVICES FOR ADMINISTERING DRUGS

(71) Applicant: AMGEN INC., Thousand Oaks, CA (US)

(72) Inventors: Margaux Frances Boyaval, Newbury Park, CA (US); Brian Stonecipher, Newbury Park, CA (US); Avon Kuo, San Jose, CA (US); James Chan, San Marino, CA (US); Lisa Nugent, Malibu, CA (US)

(73) Assignee: AMGEN INC., Thousand Oaks, CA (US)

( * ) Notice: Subject to any disclaimer, the term of this patent is extended or adjusted under 35 U.S.C. 154(b) by 800 days.

(21) Appl. No.: 17/256,249

(22) PCT Filed: Jul. 23, 2019

(86) PCT No.: PCT/US2019/042931
§ 371 (c)(1),
(2) Date: Dec. 28, 2020

(87) PCT Pub. No.: WO2020/023444
PCT Pub. Date: Jan. 30, 2020

(65) Prior Publication Data
US 2021/0369982 A1 Dec. 2, 2021

Related U.S. Application Data

(60) Provisional application No. 62/702,637, filed on Jul. 24, 2018.

(51) Int. Cl.
*A61M 5/42* (2006.01)
*A61M 5/20* (2006.01)
*A61M 5/32* (2006.01)

(52) U.S. Cl.
CPC .............. *A61M 5/422* (2013.01); *A61M 5/20* (2013.01); *A61M 5/2033* (2013.01);
(Continued)

(58) Field of Classification Search
CPC .. A61M 5/422; A61M 5/2033; A61M 5/3202; A61M 2005/2013;
(Continued)

(56) References Cited

U.S. PATENT DOCUMENTS 2,693,186 A 11/1954 Riker et al.
3,977,401 A * 8/1976 Pike .................... A61M 5/2053
604/144

(Continued)

FOREIGN PATENT DOCUMENTS

WO WO-2015048791 A1 4/2015

OTHER PUBLICATIONS

Chinese Patent Application No. 2019800482541, First Office Action, issued Jun. 22, 2022.
(Continued)

*Primary Examiner* — Tasnim Mehjabin Ahmed
(74) *Attorney, Agent, or Firm* — MARSHALL, GERSTEIN & BORUN LLP (57) ABSTRACT

Delivery devices for administering drugs are disclosed. An example apparatus, includes a body including: a handle in which a syringe assembly is to be disposed; a base having a bottom face to be disposed adjacent a user; and an absorbent material attached to the bottom face, the absorbent material structured to hold a fluid to be released onto the user prior to or during an injection procedure.

14 Claims, 3 Drawing Sheets

(52) U.S. Cl.
CPC ... *A61M 5/3202* (2013.01); *A61M 2005/2013* (2013.01); *A61M 2005/206* (2013.01); *A61M 2005/2073* (2013.01); *A61M 2205/0205* (2013.01); *A61M 2205/10* (2013.01); *A61M 2205/586* (2013.01)

(58) Field of Classification Search
CPC .... A61M 2005/206; A61M 2005/2073; A61M 2005/3267; A61M 2205/0205; A61M 2205/10; A61M 2205/586; A61M 5/20
See application file for complete search history.

(56) References Cited

U.S. PATENT DOCUMENTS

| | | | |
|---|---|---|---|
| 5,496,264 A * | 3/1996 | Watson | A61M 5/32 602/46 |
| 5,989,229 A | 11/1999 | Chiappetta | |
| 2003/0078546 A1 * | 4/2003 | Jensen | A61M 5/3202 604/232 |
| 2009/0012426 A1 | 1/2009 | Tennican | |

OTHER PUBLICATIONS

International Search Report and Written Opinion for International Application No. PCT/US2019/042931, dated Oct. 24, 2019.

\* cited by examiner

DELIVERY DEVICES FOR ADMINISTERING DRUGS

CROSS-REFERENCE TO RELATED APPLICATION

This is the United States national phase of International Patent Application No. PCT/US19/42931, filed Jul. 23, 2019, which claims priority to U.S. Provisional Patent Application No. 62/702,637, filed Jul. 24, 2018, the entire contents of each of which are hereby incorporated by reference herein.

FIELD OF THE DISCLOSURE

The present disclosure relates generally to delivery devices and, in particular, relates to delivery devices for administering drugs.

BACKGROUND

Drugs can be administered through the use of drug delivery devices such as autoinjectors or on-body injectors. Auto-injectors and on-body injectors may be used to help automate the injection and delivery or administration process, thereby simplifying the process for certain patient groups or sub-groups for which use of the syringe/vial combination or pre-filled syringe systems would be disadvantageous, whether because of physiological or psychological impediments.

Even after receiving specified training in the use of such devices, however, some patients and/or caregivers can experience challenges while using auto-injectors and/or on-body injectors. Such challenges may relate to placement of the device on the person, holding the device during an injection operation and/or removing the device after use.

Specifically, conventional autoinjectors can have an elongate, high-profile housing that requires a user to position and hold the housing through an entire injection operation without additional aid. Conversely, conventional on-body injectors can have a low-profile housing with adhesive extending across a bottom surface thereof so that the housing can be adhered to the skin of the patient for hands-free operation.

SUMMARY

In accordance with a first example, an apparatus includes a body including a handle in which a syringe assembly is configured to be disposed; a base having a bottom face configured to be disposed adjacent a user; and an absorbent material coupled with the bottom face, the absorbent material structured to hold a fluid to be released onto the user prior to or during an injection procedure.

In accordance with a second example, a drug delivery device includes a syringe assembly including a needle. The drug delivery device includes a handle carrying at least a portion of the syringe assembly. The drug delivery device includes an absorbent material having an exterior facing surface and coupled to the handle, and carrying a fluid.

In further accordance with the foregoing first and/or second examples, an apparatus and/or method may further include any one or more of the following:

In one example, the absorbent material is structured to deter the base from moving during the injection procedure.

In another example, the fluid is at least one of a sterilization fluid, a friction-generating substance, and a numbing agent.

In another example, the apparatus further includes means for deterring the fluid from evaporating prior to the injection procedure.

In another example, the apparatus further includes a housing in which the absorbent material is disposed, the housing to deter the fluid from evaporating prior to the injection procedure.

In another example, the housing includes a skin surrounding one or more sides of the absorbent material.

In another example, the apparatus includes a movement-resistant material, the movement-resistant material to surround at least a portion of the absorbent material.

In another example, the movement-resistant material includes an annular cross-section.

In another example, the apparatus further includes a release layer covering an exterior surface of the absorbent material to deter contaminants from being exposed to the absorbent material.

In another example, the syringe assembly includes a needle structured to penetrate the absorbent material prior to or during the injection procedure.

In another example, the syringe assembly includes an actuator that is structured to move a needle of the syringe assembly from a retracted position to an extended position during the injection procedure, in the extended position, the needle to extend from the base.

In another example, the actuator is triggered in response to the compressible material being compressed.

In another example, the actuator is carried at an end of the handle.

In another example, the base is structured to receive and move relative to the handle, the base including a needle guard that enables the needle to extend from the base during the injection procedure.

In another example, the apparatus further includes a spring disposed between the base and the handle to bias the needle guard toward an extended position.

In another example, further including a layer surrounding sides of the absorbent material.

In another example, the layer includes at least one of a low-tack adhesive or a non-slip coating.

In another example, further including a release liner or a removable cap covering the exterior facing surface.

In another example, the absorbent material has an open-cell arrangement and the housing has a closed-cell arrangement.

In another example, further including a needle guard carrying the absorbent material.

In another example, further including a biasing element disposed between the handle and the needle guard.

BRIEF DESCRIPTION OF THE DRAWINGS

The above needs are at least partially met through provision of the examples described in the following detailed description, particularly when studied in conjunction with the drawings, wherein.

DETAILED DESCRIPTION

The examples disclosed herein relate to delivery devices referred to as autoinjectors or hybrid autoinjectors that are structured to fit the lifestyle of a user better than some known and conventional autoinjectors or wearable on-body injectors devices. As such, based on the structure of the disclosed delivery devices, users can choose the interaction they have with the delivery device that is convenient for them. For example, a user can choose to perform an injection procedure using the example delivery devices hands-free by temporarily stabilizing a delivery device to their body or in an assisted manner that may still require some manual holding of the device. Alternatively, a user can choose to rely entirely on a manual holding of the delivery device while the injection procedure is being performed.

In examples in which the delivery device is held by the user during an injection procedure, the example delivery devices are structured to be easily held by a user with dexterity or strength challenges to substantially ensure that the injection completes successfully by increasing the grip and/or handle size of the delivery device. Put another way, the form factor of the disclosed delivery devices are structured to be easily held in place against the skin during an injection procedure. Furthermore, because the form factor of the disclosed examples is different than some known delivery devices, users may feel less stigma using the example devices because the delivery devices may be less recognizable as a drug delivery device.

Additionally or alternatively, the example delivery devices are structured to increase a foot print and/or increase the surface area interacting with the skin of the user during an injection procedure to increase stability of the delivery device. As such, the examples disclosed herein enable less adhesive, reduced strength adhesive and/or no adhesive to be used when stabilizing the delivery devices relative to the skin. Reducing and/or eliminating the use of adhesives is especially beneficial for users with thin skin or other skin issues where adhesives may cause negative reactions (e.g., pain, a rash).

Figure 1:
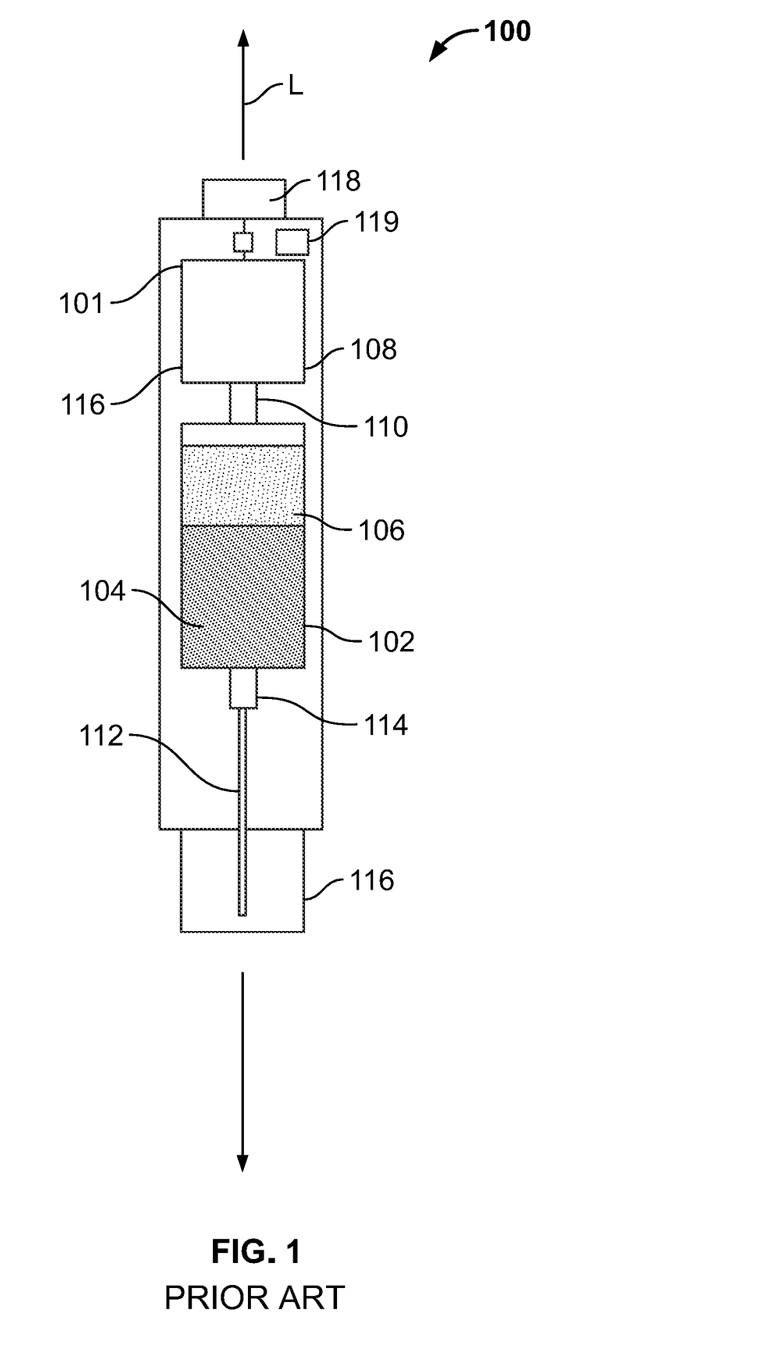
FIG. 1 is a diagrammatic view of an example autoinjector drug delivery device that can be used to implement the disclosed examples.

FIG. 1 illustrates an example delivery device 100, such as autoinjector, having a vertically oriented configuration with some or all drug delivery components disposed in stacked relation along a longitudinal axis L within a housing 101 of the delivery device 100. More specifically, in some examples, the delivery device 100 can be configured to operate and inject a user with the delivery device 100 oriented generally perpendicular to a skin surface of the user. The drug delivery components (e.g., a syringe assembly) can include a reservoir 102 having a drug/therapeutic 104 contained therein, a stopper 106 disposed within the reservoir 102 and sildably movable therein along the longitudinal axis L, a drive mechanism 108 coupled to a plunger 110 to drive the stopper 106 through the reservoir 102, a needle 112 oriented along the longitudinal axis L, a flow path 114 fluidly coupling the reservoir 102 to the needle 112 and a needle insertion mechanism 116 configured to insert the needle 112 to a desired subcutaneous depth within the user. By some approaches, the needle insertion mechanism 116 can be a retractable needle guard to expose the needle 112 or a drive mechanism to longitudinally move the needle a desired distance. For example, the drive mechanism 108 can be configured to drive both movement of the stopper 106 and the needle 112 by moving some or all of the reservoir 102, the flow path 114 and the needle 112. As commonly configured, one or more of the components of the delivery device 100, such as the drive mechanism 108 and needle insertion mechanism 116, can be operable in response to actuation of a user input device 118 accessible on an exterior of the housing 101. Suitable drive mechanisms include, but are not limited to, springs, gas sources, phase changing materials, motors or other electromechanical systems. Pursuant to this, the delivery device 100 can include electronic components, such as a controller 119, to control operation of one or more of the drug delivery components. It will be understood that although FIG. 1 shows the components centered along the longitudinal axis L, one or more of the components can be disposed off center from the longitudinal axis L within the housing 101 and still be considered to be in a stacked relation. In one example, an autoinjector drug delivery device having drug delivery components in a stacked relation corresponds to the reservoir 102 co-axially aligned with the needle 112. Example autoinjector devices are described in U.S. Ser. No. 62/447,174, filed Jan. 17, 2017, which is hereby incorporated by reference herein.

Figure 2:
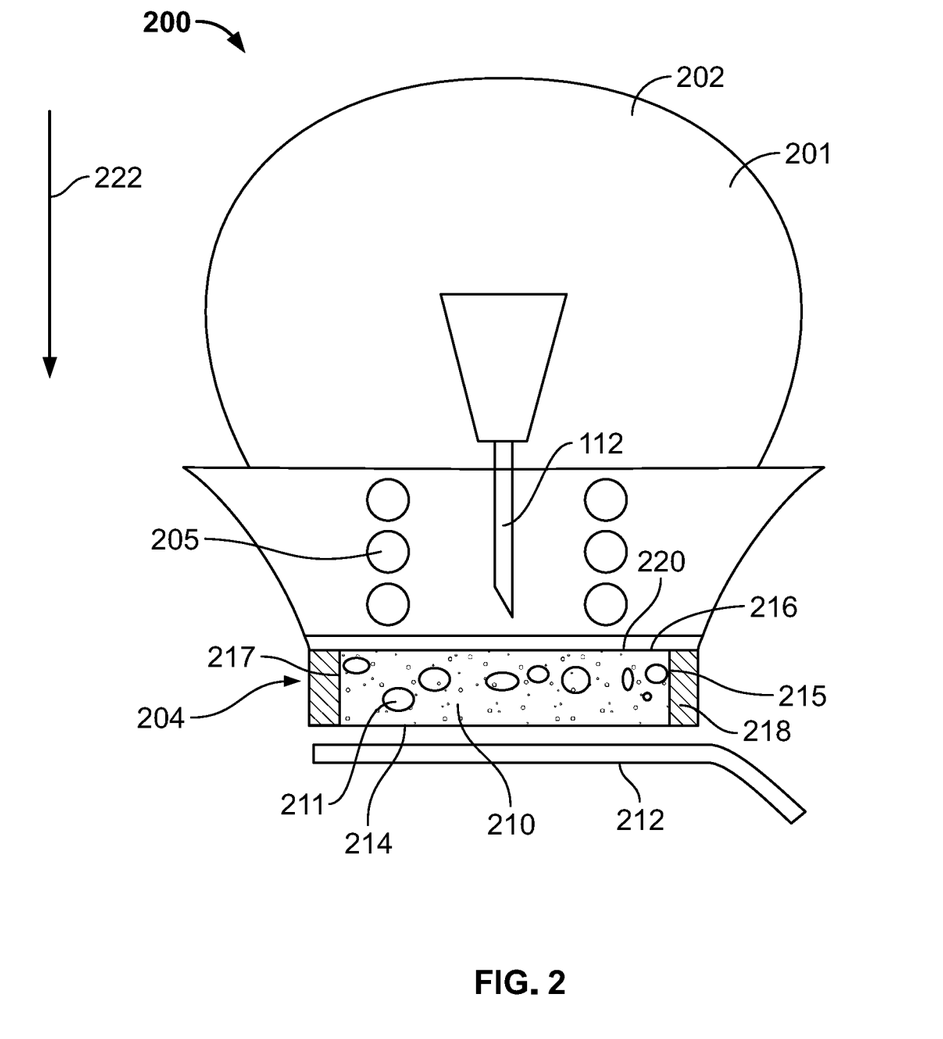
FIG. 2 illustrates an isometric view of an example delivery device in accordance with the teachings of this disclosure.

FIG. 2 illustrates an isometric view of an example delivery device 200 that can be used to administer injections in accordance with the teachings of this disclosure. In the illustrated example, the delivery device 200 includes a body 201 having a non-cylindrical shape. As shown, the body 201 includes an example handle 202 having a bulbous shape and an example base 204 toward which the handle 202 tapers. In this example, the base 204 is implemented as a needle guard biased relative to the handle 202 by a spring 205. Thus, as shown, the base 204 receives and moves relative to the handle 202 during an injection procedure to enable the needle 112 of the drug delivery components (see FIG. 1) to move toward and extend through a compressible material or layer 210 of the base 204. However, in other examples, the delivery device 200 includes an actuator that causes the needle 112 to extend through the layer 210 in response to an event occurring. In some examples, the event is associated with a threshold amount of pressure being applied to the layer 210. In other examples, the event is associated with a button carried at the end of the handle 202 being pressed. In this example, the base 204 carries the layer 210. In other examples, the layer 210 is removably coupled to the base 204 by a fastener such that a user can choose whether or not to use the layer 210. The fastener may be implemented by a snap-fit connection.

To reduce the likelihood that the delivery device 200 is inadvertently moved when a user is receiving an injection, in some examples, the layer 210 is structured to deter the base 204 from moving during an injection procedure. Additionally or alternatively, to enable the retention and selective release of a fluid or another material onto the skin prior to or during an injection procedure, in this example, the layer 210 is implemented as an absorbent material having an open-cell arrangement 211. In some examples, the fluid is a sterilization fluid (e.g., alcohol) that sterilizes the injection area. In other examples, the fluid is a friction-generating substance such as, for example, adhesive, paste, etc. that deters the delivery device 200 from moving during an injection procedure. In still other examples, the fluid is a numbing agent that numbs the injection area to decrease pain associated with the injection procedure.

To protect the layer 210 and/or to deter the fluid from evaporating, in the illustrated example, an example release liner 212 covers an exterior facing surface 214 of the layer 210 and sides 215, 216, 217 of the layer 210 are covered and/or surrounded by a side layer 218 and a top layer 220, respectively. The layers 218, 220 may be referred to as a housing in which the layer 210 is disposed. To enable the side and/or top layers 218 and/or 220 to move with the layer 210 during, for example, an injection procedure, in some examples, the side and/or top layers 218, 220 are flexible. For example, the side and/or top layers 218, 220 may be formed of a solid skin, a rubber material, another flexible material (e.g., a polymer) that deters permeation of the fluid therethrough, etc. In other words, the layers 218, 220 may be implemented by a material having a closed-cell structure.

To administer an injection using the delivery device 200 of FIG. 2, a user removes the release liner 212 from the exterior facing surface 214 and the compressible layer 210 is then positioned adjacent the skin. While this example illustrates the release liner 212 being removed from the exterior facing surface 214, in other examples, the delivery device 200 includes a cap that covers the exterior facing surface 214 prior to an injection procedure. In some such examples, the cap is coupled to the body 201 via a snap-fit connection. After the delivery device 200 is in position, the handle 202 of the delivery device 200 is moved in a direction generally indicated by arrow 222 to move the handle 202 against the force exerted by the spring 205 to move the needle 112 of the drug delivery components (see FIG. 1) toward and through the layer 210. In this example, the force exerted in the direction 222 onto the handle 202 also compresses the layer 210 and, in some instances, the associated side layer 218 causing the fluid to be released. As shown, the layer 210 is also structured to increase the relative stability and/or to deter movement of the delivery device 200 when an injection is taking place. For example, the layer 210 may be structured to release a friction-generating substance to deter the delivery device 200 from moving when an injection procedure is taking place. Additionally or alternatively, the delivery device 200 may be structured to emit sterilizing fluid, a numbing fluid, etc. While the above example illustrates the delivery device 200 being implemented as a hand-held delivery device, in other examples, the delivery device including the example compressible layer 210 can be implemented as an on-body injector. Example on body injector devices are described in U.S. Ser. No. 62/536,911, filed Jul. 25, 2017, which is hereby incorporated by reference herein.

Figure 3:
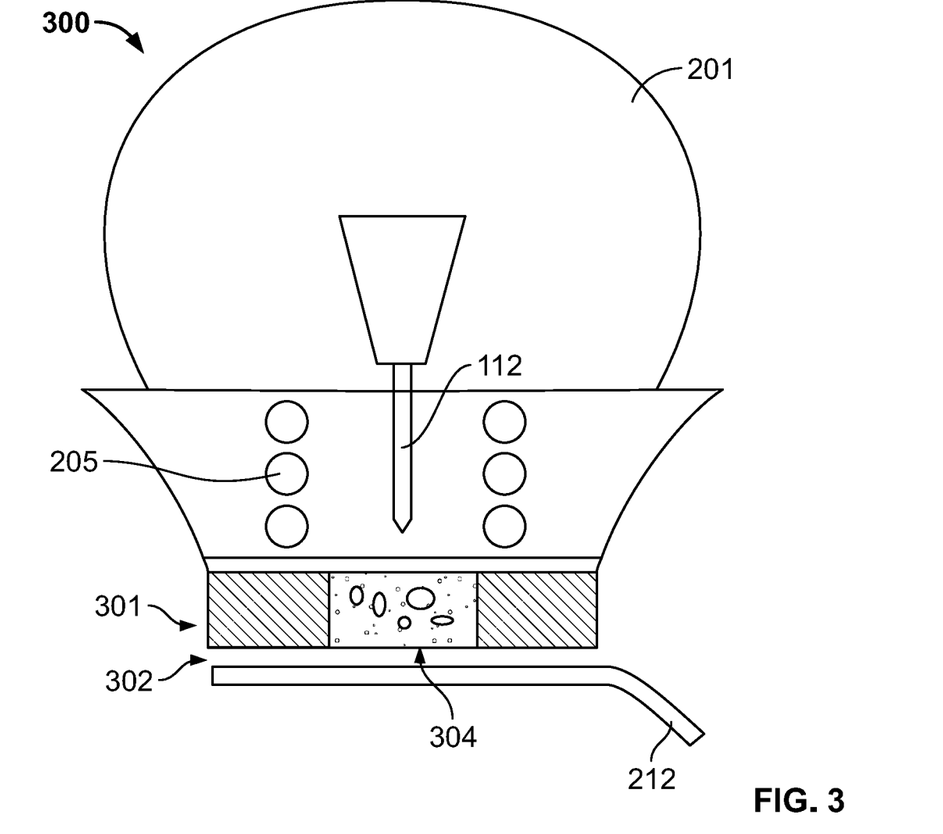
FIG. 3 illustrates a side view of another example delivery device.

FIG. 3 illustrates another example delivery device 300 that is similar to the delivery device of FIG. 2. However, in contrast to the delivery device 200 of FIG. 2, the delivery device 100 of FIG. 3 includes an example layer 301 including an example first compressible material 302 surrounded by an example second compressible material 304, where the first material 302 has movement-resistant characteristics and deters fluid from evaporating from the second material 304, and the second material 304 has absorbency characteristics enabling the second material 304 to retain and selectively dispense a fluid (e.g., a sterilization fluid). Thus, in contrast to the delivery device 200 of FIG. 2, in this example, the first material 302 implements the side layer 218 that deters the fluid from evaporating. Alternatively, the first and second materials 302, 304 may be made of the same or similar material but the first material 302 may be structured to and/or to otherwise retain less of the fluid as compared to the second material 304, enabling the first material 302 to have slip-resistant characteristics. In some examples, the layer 301 (e.g., the first material 302) includes a low-tack adhesive and/or a non-slip coating to assist in positioning the delivery device 300 relative to the skin during an injection procedure and/or to deter the delivery device 300 from moving when an injection is being administered.

Regardless of how the materials 302, 304 are implemented, an interaction between the materials 302 and/or 304 and the skin during an injection procedure deters the delivery device 300 from moving. As with other examples disclosed herein, the second compressible material 304 is structured to be penetrated by the needle 112 to enable an injection to be administered. However, in other examples, the second material 304 may define an aperture through which the needle 112 extends.

Figure 4:
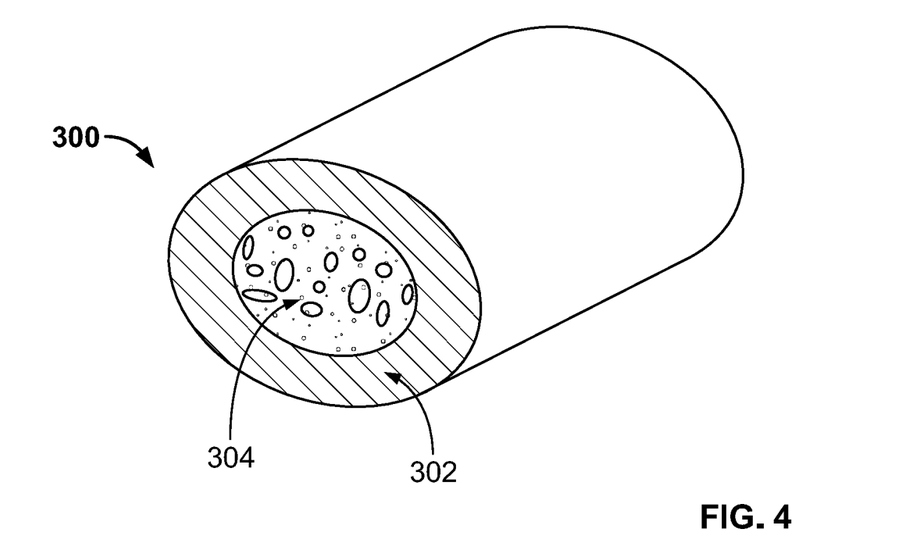
FIG. 4 illustrates an isometric bottom view of the delivery device of FIG. 3.

FIG. 4 illustrates an isometric end view of the delivery device 300 of FIG. 3. As shown in the example of FIG. 4, the first material 302 is annular and surrounds the second material 304, where the first material 302 is shown having a closed-cell arrangement to deter movement of the delivery device 300 during an injection procedure and the second material 304 is shown having an open-cell arrangement to retain and selectively release the fluid (e.g., the sterilization fluid).

The examples disclosed herein relate to example delivery devices for administering drugs having example form factors that are structured to improve the ability of the user to grip and hold the device against the skin for a threshold amount of time. Such form factors increase an ease of use even when the user has dexterity challenges. In some examples, the delivery devices are implemented as autoinjectors (e.g., hybrid autoinjectors) that are structured to be handheld when an injection is being performed and/or affixed to, for example, an appendage of the body when an injection is being performed. Moreover, the disclosed examples are structured to sanitize an injection area by dispensing sterilization fluid onto the injection area prior to and/or during an injection procedure. Such an approach increases the speed in which an injection procedure can be performed or simplifies the process by removing the typical separate step of wiping the injection area with an alcohol wipe.

When the delivery devices are implemented as an example handheld device, in some examples, the delivery devices include an example handle and a base carrying and/or including a compressible or foam-like material that is structured to reduce the likelihood that the delivery device is moved when administering an injection. In some examples, the compressible material is implemented as an absorbent material including or holding a fluid that is released when the delivery device is pressed against the skin prior to and/or during an injection procedure. In some examples, the fluid is a sterilization fluid, an adhesive, a paste, a numbing agent such as a cream and/or liquid, etc.

Advantageously, using the examples disclosed herein, a user no longer has to separately clean an injection site with an alcohol wipe because the example delivery devices are structured to sterilize the injection area by releasing the sterilization fluid when the injection procedure is taking place or prior to the injection procedure taking place. As such, an amount of time required to perform an injection procedure including the sterilization area may be reduced as compared to the time required to perform a similar procedure using known injectors.

In examples in which the material is implemented as the absorbent material, a first portion of the material may contain less of the sterilization fluid than a second portion of the material. As such, the first portion with less of the sterilization fluid may have slip-resistant properties and/or otherwise creates more friction with the skin to deter the delivery device from moving during an injection procedure. In some such examples, to reduce the likelihood that the sterilization fluid evaporates prior to the injection procedure, a layer and/or skin is positioned along the sides and the top of the material and a removable linear is coupled to the bottom of the material. In other examples, a bottom layer of the delivery device includes different materials, where a first material includes a closed-cell arrangement for enhanced gripping and/or to deter permeability and a second material includes an open-cell arrangement for absorbing and/or the storing of sterilization fluid.

Regardless of the form factor that the delivery device has and/or how the bottom layer of the base is implemented, in some examples, the delivery device includes an example syringe assembly having an example barrel that receives a plunger. In some examples, the delivery device includes an example first drive structured to move the plunger to dispense contents of the barrel. In some examples, the first drive and/or another drive is structured to move a needle of the syringe assembly from a retracted position to a deployed position. The first and/or second drives may be actuated in different ways. For example, the delivery device may carry a button that is pressed by the user and/or the drives may be activated when a threshold amount of pressure is applied at the base of the delivery device and/or when a threshold amount of pressure is applied to the sides of the delivery device.

In other examples, a needle guard is movable from an extended position in which the needle guard covers the needle to a retracted position where the need guard uncovers and/or exposes the needle. The needle guard may move from the extended position to the retracted position when a threshold amount of force is applied to the needle guard. The barrel may be referred to as a container and/or a reservoir. The needle may be associated with a cannula.

The drug delivery devices disclosed herein provide hybrid forms that advantageously provide users with additional functionalities as compared to conventional devices. In some examples, the drug delivery devices have co-axial drug delivery components such that a drug reservoir, plunger mechanism and/or needle are axially aligned. The drug delivery devices disclosed herein provide stability, gripping and/or adhesion functionalities typically associated with low profile drug delivery devices to aid users in orienting and/or supporting the device during an injection operation.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211;

2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim , G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol, 19:5138-5143); G207, 1716; NV1020; NV12023; NV1034 and NV1042 (Varghes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The invention claimed is:

1. An apparatus, comprising:
    a body including:
        a handle in which a syringe assembly is configured to be disposed;
        a base having a bottom face configured to be disposed adjacent a user; and
        an absorbent material coupled with the bottom face, the absorbent material structured to hold a fluid to be released onto the user prior to or during an injection procedure,
    wherein the absorbent material is structured to deter the base from moving during the injection procedure,
    wherein the fluid is at least one of: (a) a sterilization fluid, (b) a friction-generating substance, and (c) a numbing agent, and
    further including a housing in which the absorbent material is disposed, the housing to deter the fluid from evaporating prior to the injection procedure.

2. The apparatus of claim 1, wherein the housing includes a housing skin surrounding one or more sides of the absorbent material.

3. The apparatus of claim 1, further including a movement-resistant material, the movement-resistant material to surround at least a portion of the absorbent material.

4. The apparatus of claim 3, wherein the movement-resistant material includes an annular cross-section.

5. The apparatus of claim 1, further including a release layer covering an exterior surface of the absorbent material to deter contaminants from being exposed to the absorbent material.

6. The apparatus of claim 1, further comprising the syringe assembly, wherein the syringe assembly includes a needle structured to penetrate the absorbent material prior to or during the injection procedure.

7. The apparatus of claim 1, further comprising the syringe assembly, wherein the syringe assembly includes an actuator that is structured to move a needle of the syringe assembly from a retracted position to an extended position during the injection procedure, in the extended position, the needle to extend from the base.

8. The apparatus of claim 7, wherein the actuator is triggered in response to the absorbent material being compressed or the actuator is carried at an end of the handle.

9. The apparatus of claim 1, wherein the base is structured to receive and move relative to the handle, the base including a needle guard that enables the needle to extend from the base during the injection procedure.

10. The apparatus of claim 9, further including a spring disposed between the base and the handle to bias the needle guard toward an extended position.

11. The apparatus of claim 1, the housing comprising a layer surrounding sides of the absorbent material, wherein the layer includes at least one of a low-tack adhesive or a non-slip coating.

12. The apparatus of claim 1, wherein the absorbent material has an open-cell arrangement.

13. The apparatus of claim 1, further comprising a needle guard carrying the absorbent material.

14. The apparatus of claim 13, further comprising a biasing element disposed between the handle and the needle guard.

* * * * *